United States Patent [19]

Fuchigami et al.

[11] Patent Number: 4,927,971

[45] Date of Patent: May 22, 1990

[54] DESENSITIZER COMPOSITION

[75] Inventors: Mitsuru Fuchigami; Shingo Tachizawa, both of Takasago; Mamoru Ishiguro, Tokyo, all of Japan

[73] Assignee: Mitsubishi Paper Mills Ltd., Tokyo, Japan

[21] Appl. No.: 348,687

[22] Filed: May 8, 1989

[30] Foreign Application Priority Data

| | | | |
|---|---|---|---|
| May 11, 1988 | [JP] | Japan | 63-115724 |
| May 11, 1988 | [JP] | Japan | 63-115725 |
| May 11, 1988 | [JP] | Japan | 63-115726 |
| Jun. 7, 1988 | [JP] | Japan | 63-141264 |
| Jul. 22, 1988 | [JP] | Japan | 63-183100 |
| Dec. 28, 1988 | [JP] | Japan | 63-335233 |

[51] Int. Cl.5 .......... C07C 93/04

[52] U.S. Cl. .......... 564/505; 564/463; 564/512

[58] Field of Search .......... 564/505, 463, 512

[56] References Cited

U.S. PATENT DOCUMENTS

| | | | |
|---|---|---|---|
| 2,777,780 | 1/1957 | Cormack et al. | 503/201 |
| 4,036,881 | 7/1977 | Brennan et al. | 564/512 |
| 4,705,834 | 11/1987 | Baur et al. | 564/505 |
| 4,726,909 | 2/1988 | Otten et al. | 564/505 |
| 4,747,851 | 5/1988 | Sung et al. | 564/505 |

FOREIGN PATENT DOCUMENTS

| | | |
|---|---|---|
| 2359079 | 11/1973 | Fed. Rep. of Germany . |
| 2343800 | 3/1974 | Fed. Rep. of Germany . |
| 2361856 | 6/1974 | Fed. Rep. of Germany . |
| 44-27255 | 11/1969 | Japan . |
| 45-21448 | 7/1970 | Japan . |
| 46-22651 | 6/1971 | Japan . |
| 46-29546 | 8/1971 | Japan . |
| 47-38201 | 9/1972 | Japan . |
| 47-32915 | 11/1972 | Japan . |
| 48-6805 | 1/1973 | Japan . |
| 49-4484 | 2/1974 | Japan . |
| 49-15513 | 2/1974 | Japan . |
| 49-43708 | 4/1974 | Japan . |
| 49-19647 | 5/1974 | Japan . |
| 49-23008 | 6/1974 | Japan . |
| 49-23850 | 6/1974 | Japan . |
| 49-72009 | 7/1974 | Japan . |
| 49-77709 | 7/1974 | Japan . |
| 49-77710 | 7/1974 | Japan . |
| 49-83509 | 8/1974 | Japan . |
| 58-38119 | 8/1983 | Japan . |
| 63-41184 | 2/1988 | Japan . |

*Primary Examiner*—Richard L. Raymond
*Assistant Examiner*—Raymond Covington
*Attorney, Agent, or Firm*—Cushman, Darby & Cushman

[57] ABSTRACT

There is disclosed a desensitizing ink comprising an adduct produced by the addition of 4 to 70 mols of an alkylene oxide to 1 mol of an amine represented by the general formula (I) where 40 mol % or more of said alkylene oxide are butylene oxide:

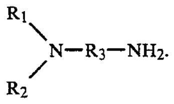

(I)

8 Claims, No Drawings

DESENSITIZER COMPOSITION

BACKGROUND OF THE INVENTION

1. Field of the Invention

The present invention relates to a desensitizing ink for use in pressure sensitive manifold sheets and more particularly, to a desensitizing ink for use in such pressure sensitive manifold sheets which exhibits no blurring with water, a great versatility in various printings, an improved desensitizing effect and set-off property.

2. Description of Related Art

It has been long recognized that colored images can be produced by a reaction between a colorless electron-donating or proton-withdrawing organic compound (referred to as "coupler" hereinafter) and an electron-withdrawing or proton-donating compound (referred to as "developer" hereinafter). As products making use of this phenomenon in practice, one may mention pressure sensitive copy sheets (see e.g., U.S. Pat. Nos. 2,505,470; 2,505,489; 2,550,471; 2,548,366; 2,712,507; 2,730,456; 2,730,457; 3,418,250; 3,672,935), and thermo-sensitive copy sheets (see, e.g., Japanese Patent Examined Publication Nos. S.43-4160; S.43-7600; S.45-14039; U.S. Pat. No. 2,939,009). Moreover, a method for producing colored images by applying an ink containing a coupler to a sheet coated with a developer also has been known [German patent application (OLS) No. 1939962].

Developers having the properties as defined above include clays, phenol resins, metal salts of aromatic carboxylic acids and the like.

Generally, in pressure sensitive manifold sheets, a combination of a layer having microcapsules containing said coupler and a developer layer has been used to produce colored images by superimposing one over the other, applying writing or typing pressures to the manifold sheets to collapse the microcapsules whereby the coupler and the developer will come to contact with each other.

Generally, the developers are uniformly coated all over the surface of a support sheet in use. When the developer sheets should have certain parts where desired to have nothing recorded depending on the purpose of the use of pressure sensitive manifold sheets, an attempt has been employed to apply a desensitizing ink containing a desensitizer on parts by a printing machine.

Desensitizing inks to be used for such purpose are described in detail, for example, in U.S. Pat. No. 2,777,780: Japanese Patent Examined Publication Nos. S.44-27255; S.45-21448; S.46-22651; S.46-29546: Japanese Patent Unexamined Publication Laid-Open No. S.47-32915: Japanese Patent Examined Publication Nos. S.47-38201; S.48-4050: Japanese Patent Unexamined Publication Laid-Open No. S.48-6805: Japanese Patent Examined Publication Nos. S.49-4484; S.49-19647; S.49-23008; S.49-23850: Japanese Patent Unexamined Publication Laid-Open Nos. S.49-43708; S.49-72009; S.49-77709; S.49-77710; S.49-15513; S.49-83509; German patent application (OLS) Nos. 2343800; 2359079; 2361856: Japanese Patent Examined Publication No. S.58-38119; Japanese Patent Unexamined Publication Laid-Open Nos. S.63-74681; S.63-41184.

Thus, the printing inks as mentioned above comprise generally desensitizers, pigments such as titanium dioxide, binders, and if necessary, diluents such as organic solvents. However, no desensitizing ink having excellent desensitizing effects on various developers and good off-set property has not been obtained. In addition, the use of desensitizers having a higher water solubility may cause blurring with water, or conversely the use of water insoluble desensitizers may not achieve uniformly printed areas when employed in offset printing. That is, the opposite properties have been imparted.

SUMMARY OF THE INVENTION

It is an object of the present invention to provide a desensitizer having an adequate desensitizing ability and causing little practical difficulties and a copy sheet using a desensitizer.

That is, the present invention relates to a desensitizing ink for use in pressure sensitive manifold sheets which has an excellent print adaptability, remarkable desensitizing effect on various developers, good set-off property and no tendency to cause blurring with water.

DETAILED DESCRIPTION OF PREFERRED EMBODIMENTS

The present invention is directed to a desensitizing ink containing desensitizers, pigments and binders, using an alkylene oxide adduct of an amine compound represented by the general formula:

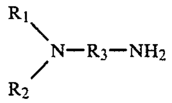

(I)

More particularly, the present invention is directed to an adduct of 4 to 70 mols of alkylene oxide to 1 mol of an amine represented by the general formula (I) where 40 mol % or more of the alkylene oxide are butylene oxide:

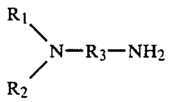

(I)

where $R_1$ and $R_2$ represent hydrogen or an alkyl group having 1 to 20 carbon atoms;

when both $R_1$ and $R_2$ are hydrogen atoms, $R_3$ represents a branched alkylene having 3 to 9 carbon atoms, or a substituted alkylene represented by the general formula (II) or (III):

$$-CnH_2n-\underset{H}{N}-C_2H_4-(\underset{H}{N}-CnH_2n)_m \quad (II)$$

where m is 0 or 1, n is an integer of 3 to 6, $$-(CH_2)_l\underset{CH_3}{\underset{|}{N}}-(CH_2)_l \quad (III)$$

where l is an integer of 1 to 4;

when both $R_1$ and $R_2$ are alkyl groups having 1 to 20 carbon atoms, $R_3$ represents an alkylene group represented by the general formula (IV):

$$-(CH_2)_q \quad (IV)$$

where q is an integer of 1 to 12.

In an embodiment, one may mention those in which $R_1$ and $R_2$ are hydrogen atoms and the branched alkylene is represented by the general formula (V):

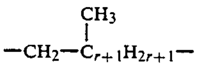
(V)

where r is an integer of 0 to 6.

In an preferred embodiment, those in which the branched alkylene represented by the general formula (V) is selected from a group consisting of:

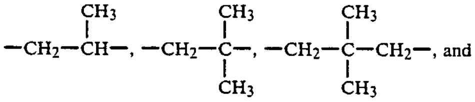
and

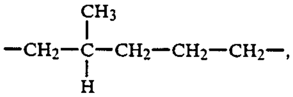
or those in which both $R_1$ and $R_2$ in the general formula (I) are hydrogen atoms and the alkylene represented by the general formula (III) is:

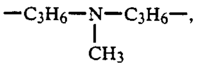
or those in which both $R_1$ and $R_2$ in the general formula (I) are hydrogen atoms, and alkylene group represented by the general formula (II) is:

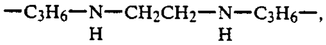
or those in which both $R_1$ and $R_2$ in the general formula (I) are alkyl group, and alkylene group represented by the general formula (IV) is $-C_2H_4-$ or $-C_3H_6-$, or more particularly those in which both $R_1$ and $R_2$ are selected from a group consisting of $CH_3-$, $C_2H_5-$, $C_3H_7-$, $C_4H_9-$.

The alkylene oxide adduct of an amine compound above-mentioned may be obtained by the addition of 1 mol of amine compound represented by the general formula (I) with 4 to 70 mols of alkylene oxide where 40 mol % or more of the alkylene oxide are butylene oxide.

Although 40 mol % or more of the alkylene oxide must be butylene oxide, the remaining 60% or less can be ethylene oxide, butylene oxide, propylene oxide, styrene oxide and the like, preferably, propylene oxide or butylene oxide.

The adduct as defined above may be produced through the methods as disclosed in U.S. Pat. Nos. 2,695,314, or 3,152,188 using amines represented by the general formula (I) and alkylene oxide.

Examples of amine compound represented by the general formula (I) to be used preferably in the present invention include the followings:

I. those where in the general formula (I) both $R_1$ and $R_2$ are hydrogen atoms and $R_3$ is a branched alkylene having 3 to 9 carbon atoms, more particularly, $R_3$ is an alkylene having the general formula (V) such as:

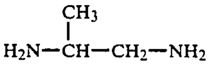
(1)

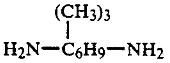
(2)

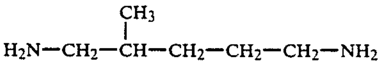
(3)

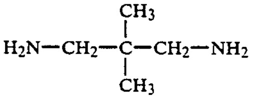
(4)

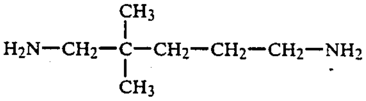
(5)

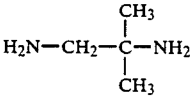
(6)

II. those where in the general formula (I) both $R_1$ and $R_2$ are hydrogen atoms and $R_3$ is represented by the general formula (III) such as:

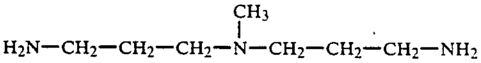
(1)

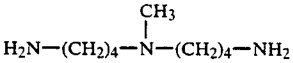
(2)

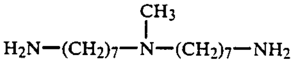
(3)

III. those where in the general formula (I), at least either $R_1$ or $R_2$ is an alkyl group having 1 to 20 carbon atoms and $R_3$ is an alkylene represented by the general formula (IV), more particularly, both $R_1$ and $R_2$ are alkyl having 1 to 20 carbon atoms and $R_3$ is an alkylene having 1 to 5 carbon atoms such as:

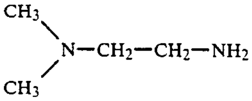
(1)

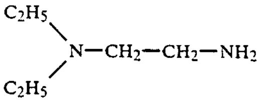
(2)

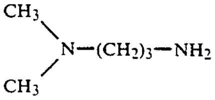
(3)

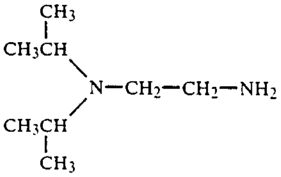
(4)

-continued

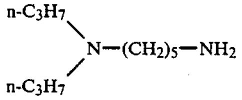 (5)

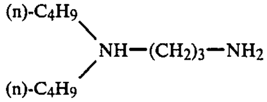 (6)

IV. those where in the general formula (I), both $R_1$ and $R_2$ are hydrogen atoms and $R_3$ is represented by the general formula (II) such as:

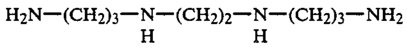 (1)

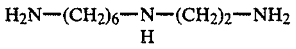 (2)

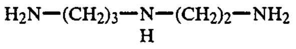 (3)

The aforementioned amines contain generally isomers and the like as impurities when they are commercially available. The impurity-containing ones may be put in use as they are, or a mixture of two or more amines may be employed.

As adducts, one may mention the followings:

I a. adducts of amine compounds where in the general formula (I), both $R_1$ and $R_2$ are hydrogen atoms and $R_3$ is a branched alkylene group having 3 to 9 carbon atoms, are exemplified as follows (where BO and PO represent oxybutylene and oxypropylene, respectively):

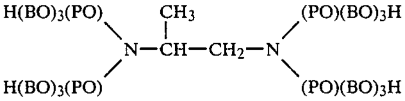 1.

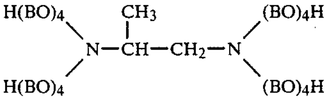 2.

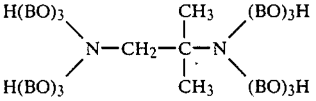 3.

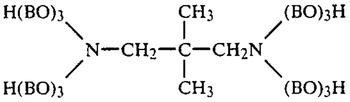 4.

-continued

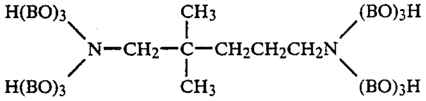 5.

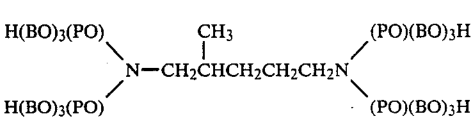 6.

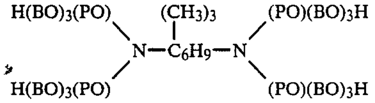 7.

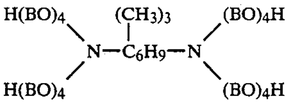 8.

II a. adducts of amine compounds where in the general formula (I), both $R_1$ and $R_2$ are hydrogen atoms and $R_3$ is represented by the general formula (III) are exemplified as follows:

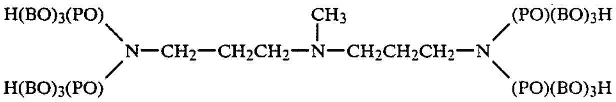

and

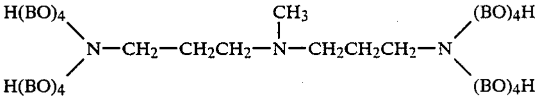

III a. adducts of amine compounds where in the general formula (I), at least either $R_1$ or $R_2$ is, preferably both of them are alkyl and $R_3$ is an alkylene group represented by the general formula (IV), exemplified as follows:

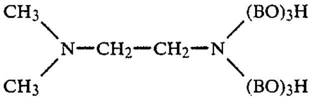 1.

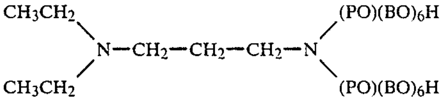 2.

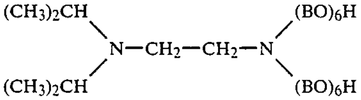 3.

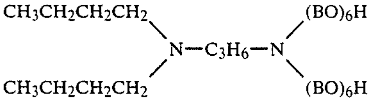 4.

IV a. adducts of amine compounds where in the general formula (I), both $R_1$ and $R_2$ are hydrogen atoms and $R_3$ is represented by the general formula (II), are exemplified as follows:

1.

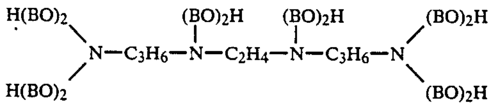

2.

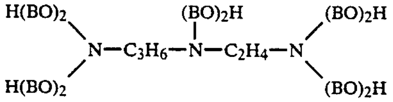

3.

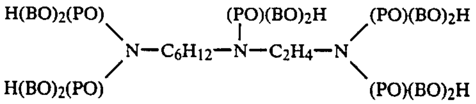

The aforementioned desensitizers may be employed as alone, a mixture of two or more, or in combination with known desensitizers.

Pigments used in the present invention claimed include white pigments such as titanium dioxide, barium sulfate, calcium carbonate, talc, kaolin, bentonite and the like.

Binders used in the present invention claimed include natural or synthetic high molecular compounds such as rosin modified phenolic resin, ketone resin, polyamide resin, maleic resin, phenolic resin, epoxy resin, alkyd resin, melamine resin, urea resin, nitrocellulose, ethylcellulose, butyral resin, polyvinyl alcohol, gelatin, shellac and the like.

A desensitizing ink of the present invention claimed may be used as the aforementioned composition alone, or if necessary, together with diluents such as organic solvents. Organic solvents include, for example, linseed oil, tung oil, soybean oil, cottonseed oil, methanol, ethanol, ethyl acetate, toluene, hexane, methyl ethyl ketone, methyl isobutyl ketone, polypropylene glycol, polybutylene glycol, paraffinic oil and the like.

A desensitizing ink of the present invention claimed may contain, if necessary, waxes such as paraffin wax, microcrystalline wax, carnaubawax, offset inhibitors such as starch, dextrin, ultraviolet absorber, antioxidant, and the like.

The present invention will be illustrated by the following Examples. It is not intended that the present invention is restricted by those Examples.

EXAMPLES 1 TO 2 AND COMPARATIVE EXAMPLES 1 TO 2

To 40 parts by weight of desensitizers shown in Table 1, 17 parts by weight of rosin modified phenolic resin (Tamanol T 135, manufactured by Alakawa Kagaku Co.) were added, and the whole was melted at a temperature of 150° C. After the melt was cooled down to a temperature of 25° C., 25 parts by weight of the titanium dioxide and 18 parts by weight of white spindle oil were added to the melt. The resulting mixture was kneaded with a triple roller mill to produce desensitizing inks for use in offset and letterpress.

Manifold sheets used in the test were the inner sheets of commercially available pressure sensitive manifold sheets (Fujipressure sensitive manifold sheets supplied by Fuji Shashin Film Co.).

The ink was evaluated by the test where 3 g/m$^2$ of the desensitizing ink was printed on a sheet which was placed on a innersheet under a loading of 100 g/cm$^2$ for a week. An extent of the transfer of the ink of the inner sheet was evaluated as offset property. Moreover, a top sheet (from commercially available Fuji pressure sensitive manifold sheets) was superimposed on the printed surface and then overall color development was effected with a supercalender to evaluate "desensitizing effect" and "uniformity" of the desensitizing effect. The results are shown in Table 2.

TABLE 1

Example 1

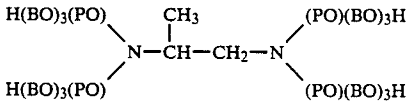

Example 2

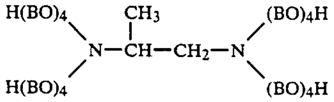

Comparative Example 1

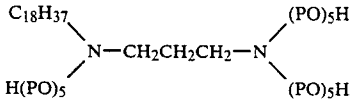

Comparative Example 2

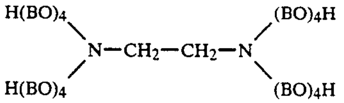

TABLE 2

| | Printing Machine | (Results) Set-off | Desensitizing Effect | Uniformity |
|---|---|---|---|---|
| Example 1 | Offset | O | O | O |
| Example 1 | Letterpress | O | O | O |
| Example 2 | Offset | O | O | O |
| Comparative Example 1 | Offset | — | — | X |
| Comparative Example 1 | Letterpress | Δ | Δ~O | Δ~O |
| Comparative Example 2 | Offset | Δ | Δ~O | Δ |

O: superior
Δ: less superior
X: inferior

EXAMPLES 3 TO 17 AND COMPARATIVE EXAMPLES 3 TO 12

Desensitizing inks were prepared in the same manner as in Examples 1 to 2 except that adducts shown in Table 3 were used, and evaluated by the same procedure as in Examples 1 to 2. The results are shown in Table 4.

TABLE 3
Example 3*
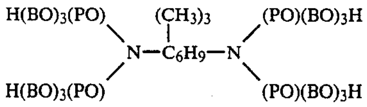
Example 4*
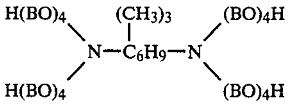
Comparative Example 3
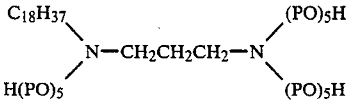
Comparative Example 4
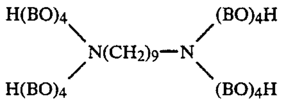
Example 5
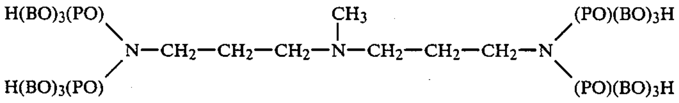
Example 6
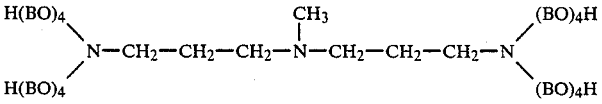
Comparative Example 5
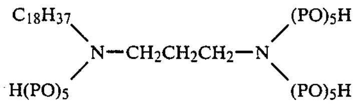
Comparative Example 6
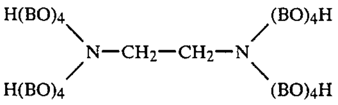
Example 7
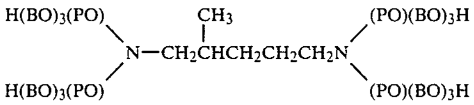
Example 8
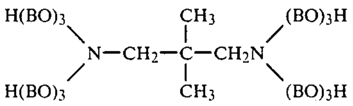

TABLE 3-continued
Example 9
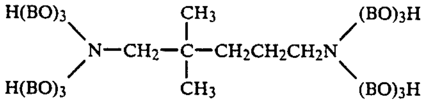
Example 10
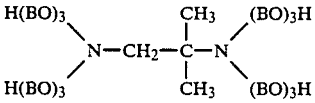
Comparative Example 7
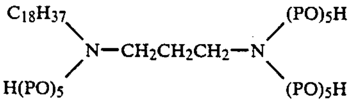
Comparative Example 8
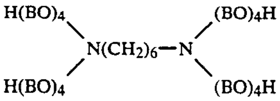
Example 11
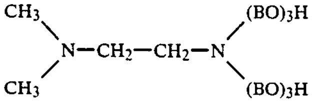
Example 12
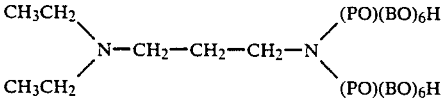
Example 13
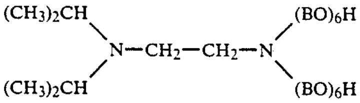
Example 14
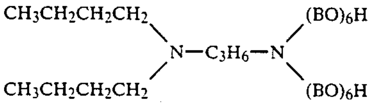
Comparative Example 9
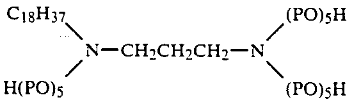
Comparative Example 10
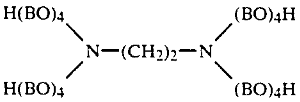

TABLE 3-continued

Example 15

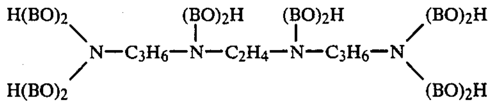

Example 16

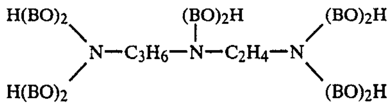

Example 17

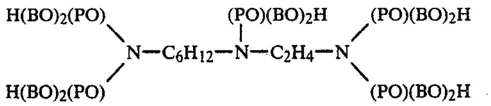

Comparative Example 11

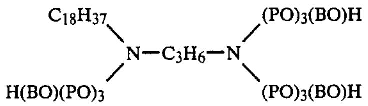

Comparative Example 12

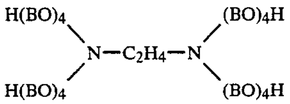

(Note)
*In Examples 3 and 4, starting materials used for producing the adducts were mixtures of 2,2,4-trimethylhexamethylenediamine and 2,4,4-trimethylhexamethylenediamine (commercially available as TMD).

TABLE 4

| | | (Results) | | |
|---|---|---|---|---|
| | Printing Machine | Set-off | Desensitizing Effect | Uniformity |
| Example 3 | Offset | O | O | O |
| Example 3 | Letterpress | O | O | O |
| Example 4 | Offset | O | O | O |
| Comparative Example 3 | Offset | — | — | X |
| Comparative Example 3 | Letterpress | Δ | Δ~O | Δ~O |
| Comparative Example 4 | Offset | Δ | Δ~O | Δ |
| Example 5 | Offset | O | O | O |
| Example 5 | Letterpress | O | O | O |
| Example 6 | Offset | O | O | O |
| Comparative Example 5 | Offset | — | — | X |
| Comparative Example 5 | Letterpress | Δ | Δ~O | Δ~O |
| Comparative Example 6 | Offset | Δ | Δ~O | Δ |
| Example 7 | Offset | O | O | O |
| Example 7 | Letterpress | O | O | O |
| Example 8 | Offset | O | O | O |
| Example 9 | Offset | O | O | O |
| Example 10 | Offset | O | O~◎ | O |
| Comparative Example 7 | Offset | — | — | X |
| Comparative Example 7 | Letterpress | Δ | Δ~O | Δ~O |
| Comparative Example 8 | Offset | Δ | Δ~O | Δ |
| Example 11 | Offset | O | O~◎ | O |
| Example 11 | Letterpress | O | O | O |
| Example 12 | Offset | O | O | O |
| Example 13 | Offset | O | O | O |
| Example 14 | Offset | O | O | O |

TABLE 4-continued

| | | (Results) | | |
|---|---|---|---|---|
| | Printing Machine | Set-off | Desensitizing Effect | Uniformity |
| Comparative Example 9 | Offset | X | — | — |
| Comparative Example 9 | Letterpress | Δ~O | Δ~O | Δ |
| Comparative Example 10 | Offset | Δ | Δ~O | X |
| Example 15 | Offset | O | O | O |
| Example 15 | Letterpress | O | O | O |
| Example 16 | Offset | O | O | O |
| Example 17 | Offset | O | O | O |
| Comparative Example 11 | Offset | — | — | X |
| Comparative Example 11 | Letterpress | Δ | Δ~O | Δ~O |
| Comparative Example 12 | Offset | Δ | Δ~O | Δ |

(Note)
◎: especially superior,
Δ: less inferior,
O: superior,
X: inferior,

As illustrated above, the desensitizing inks of the present invention claimed have excellent adaptability in printings, setoff property and desensitizing effect.

What is claimed is:

1. A desensitizing ink comprising an adduct produced by the addition of 4 to 70 mols of an alkylene oxide to 1 mol of an amine represented by the general formula (I) where 40 mol % or more of said alkylene oxide are butylene oxide:

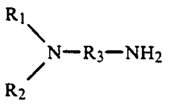

(I)

where $R_1$ and $R_2$ represent hydrogen atoms or an alkyl group having 1 to 20 carbon atoms;

when both $R_1$ and $R_2$ are hydrogen atoms, $R_3$ represents a branched alkylene having 3 to 9 carbon atoms, or a substituted alkylene represented by the general formula (II) or (III):

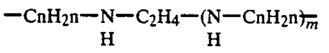

(II)

where m is 0 or 1, n is an integer of 3 to 6,

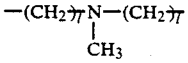

(III)

where l is an integer of 1 to 4, when at least either $R_1$ or $R_2$ is an alkyl group having 1 to 20 carbon atoms, $R_3$ represents an alkylene group represented by the general formula (IV):

$-(CH_2)_q-$ (IV)

where q is an integer of 1 to 12.

2. A desensitizing ink of claim 1 where said branched alkylene having 3 to 9 carbon atoms is represented by the general formula (V):

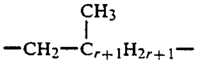

(V)

where r is an integer of 0 to 6.

3. A desensitizing ink of claim 2 where said branched alkylene represented by the general formula (V) is:

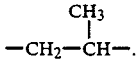

4. A desensitizing ink of claim 2 where said branched alkylene represented by the general formula (V) is selected from a group consisting of:

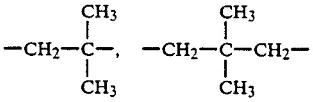

and

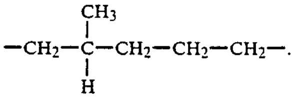

5. A desensitizing ink of claim 1 where both $R_1$ and $R_2$ in the general formula (I) are hydrogen atoms and said alkylene represented by the general formula (III) is:

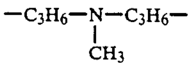

6. A desensitizing ink of claim 1 where both $R_1$ and $R_2$ in the general formula (I) are hydrogen atoms and said alkylene represented by the general formula (II) is:

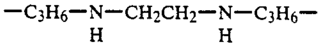

7. A desensitizing ink of claim 1 where both $R_1$ and $R_2$ in the general formula (I) are alkyl and said alkylene represented by the general formula (IV) is selected from a group consisting of:

$-C_2H_4-$ and $-C_3H_6-$.

8. A desensitizing ink of claim 7 where both $R_1$ and $R_2$ are selected from a group consisting of:

$CH_3-$, $C_2H_5-$, $C_3H_7-$, $C_4H_9-$.

* * * * *